(12) United States Patent
Srinivasan et al.

(10) Patent No.: US 9,914,651 B2
(45) Date of Patent: Mar. 13, 2018

(54) CURRENT EFFICIENT ELECTROLYTIC DEVICE AND METHOD

(71) Applicants: Kannan Srinivasan, Tracy, CA (US); Christopher A. Pohl, Union City, CA (US); Sheetal Bhardwaj, Fremont, CA (US); Rong Lin, Santa Clara, CA (US)

(72) Inventors: Kannan Srinivasan, Tracy, CA (US); Christopher A. Pohl, Union City, CA (US); Sheetal Bhardwaj, Fremont, CA (US); Rong Lin, Santa Clara, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 416 days.

(21) Appl. No.: 13/890,029

(22) Filed: May 8, 2013

(65) Prior Publication Data

US 2014/0332387 A1 Nov. 13, 2014

(51) Int. Cl.
*C02F 1/00* (2006.01)
*C02F 1/34* (2006.01)
(Continued)

(52) U.S. Cl.
CPC ............. *C02F 1/4695* (2013.01); *B01J 39/26* (2013.01); *B01J 41/20* (2013.01); *B01J 47/12* (2013.01); *B01J 49/30* (2017.01); *G01N 30/56* (2013.01); *G01N 30/96* (2013.01); *G01N 2030/562* (2013.01); *G01N 2030/965* (2013.01)

(58) Field of Classification Search
CPC ........ B01D 15/00; B01D 15/08; B01D 15/10; B01D 35/06; B01D 61/00; B01D 62/42; B01D 61/46; B01D 61/48; B01D 61/52; B01D 61/445; B01D 69/00; B01D 71/00; B01J 20/00; B01J 20/32; B01J 39/26; B01J 41/20; B01J 47/08; B01J 49/0052; B01J 2220/54; C02F 1/40; C02F 1/42; C02F 1/469; C02F 1/4604; C02F 1/4695
USPC ...... 204/182, 182.3, 182.4, 182.5, 237, 301, 204/450, 518, 520, 522, 523, 524, 536, 204/539, 542, 630, 632, 638, 639; 205/334; 210/96.1, 198.1, 198.2, 200, 210/243, 257.2, 259, 266, 294, 321.1, 210/321.2, 541, 635, 638, 644, 656, 659, 210/662, 663, 681, 746, 748.01; 214/182.4, 182.6; 422/70, 535
See application file for complete search history.

(56) References Cited

U.S. PATENT DOCUMENTS 4,265,634 A 5/1981 Pohl
4,290,775 A 9/1981 Stevens et al.
(Continued)

FOREIGN PATENT DOCUMENTS

CN 1403811 3/2003
CN 1744945 3/2006
(Continued)

OTHER PUBLICATIONS

U.S. Appl. No. 13/674,738, filed Nov. 12, 2012, to Srinivasan.
(Continued)

*Primary Examiner* — Hayden Brewster

(57) ABSTRACT

A sandwich suppressor in an ion chromatography system in which loosely packed ion exchange resin of low density is disposed in the central sample stream flow channel. Also, a method of using the suppressor is described.

20 Claims, 8 Drawing Sheets

(51) Int. Cl.

| | | |
|---|---|---|
| *C02F 1/48* | (2006.01) | |
| *C02F 1/469* | (2006.01) | |
| *G01N 30/56* | (2006.01) | |
| *G01N 30/96* | (2006.01) | |
| *B01J 39/26* | (2006.01) | |
| *B01J 41/20* | (2006.01) | |
| *B01J 47/12* | (2017.01) | |
| *B01J 49/30* | (2017.01) | |
| *B01D 15/00* | (2006.01) | |
| *B01D 15/08* | (2006.01) | |
| *B01J 47/08* | (2006.01) | |

(56) References Cited

U.S. PATENT DOCUMENTS

| | | | |
|---|---|---|---|
| 4,474,664 A | 10/1984 | Stevens et al. | |
| 4,751,189 A | 6/1988 | Rocklin | |
| 4,999,098 A | 3/1991 | Pohl et al. | |
| 5,045,204 A | 9/1991 | Dasgupta et al. | |
| 5,248,246 A | 9/1993 | Lew et al. | |
| 5,248,426 A | 9/1993 | Stillian et al. | |
| 5,352,360 A | 10/1994 | Stillian et al. | |
| 5,518,622 A | 5/1996 | Stillian et al. | |
| 5,569,365 A | 10/1996 | Rabin et al. | |
| 5,597,481 A | 1/1997 | Stillian et al. | |
| 5,597,734 A | 1/1997 | Small et al. | |
| 5,773,615 A | 6/1998 | Small et al. | |
| 5,788,826 A * | 8/1998 | Nyberg | B01J 47/08 |
| | | | 204/536 |
| 6,077,434 A | 6/2000 | Srinivasan et al. | |
| 6,325,976 B1 | 12/2001 | Small et al. | |
| 6,328,885 B1 | 12/2001 | Srinivasan et al. | |
| 6,425,284 B1 | 7/2002 | Srinivasan et al. | |
| 6,436,719 B1 | 8/2002 | Srinivasan et al. | |
| 6,495,371 B2 | 12/2002 | Small et al. | |
| 6,508,985 B2 | 1/2003 | Small et al. | |
| 6,610,546 B1 | 8/2003 | Liu et al. | |
| 7,399,415 B2 | 7/2008 | Srinivasan et al. | |
| 7,517,696 B2 | 4/2009 | Srinivasan et al. | |
| 7,524,457 B2 | 4/2009 | Srinivasan et al. | |
| 8,216,515 B2 | 7/2012 | Liu et al. | |
| 8,333,891 B2 | 12/2012 | Wyatt | |
| 8,415,168 B2 | 4/2013 | Liu et al. | |
| 2005/0034997 A1* | 2/2005 | DiMascio et al. | 205/556 |
| 2005/0258360 A1 | 11/2005 | Whitehouse et al. | |
| 2006/0057733 A1 | 3/2006 | Liu et al. | |
| 2006/0186046 A1 | 8/2006 | Liu et al. | |
| 2006/0254969 A1 | 11/2006 | Yamanaka et al. | |
| 2007/0051684 A1 | 3/2007 | Grebenyuk et al. | |
| 2007/0062873 A1 | 3/2007 | Liu et al. | |
| 2008/0053830 A1 | 3/2008 | Tsonev et al. | |
| 2008/0314750 A1 | 12/2008 | Hagner-McWhirter et al. | |
| 2009/0127200 A1 | 5/2009 | Dasgupta et al. | |
| 2009/0166293 A1* | 7/2009 | Srinivasan | B01D 15/367 |
| | | | 210/656 |
| 2009/0308757 A1 | 12/2009 | Crettenand | |
| 2013/0306565 A1* | 11/2013 | Davis | 210/675 |
| 2014/0134050 A1 | 5/2014 | Srinivasan et al. | |
| 2014/0332387 A1 | 11/2014 | Srinivasan et al. | |

FOREIGN PATENT DOCUMENTS

| | | |
|---|---|---|
| CN | 101952717 A | 1/2011 |
| CN | 103969378 A | 8/2014 |
| EP | 0032770 B1 | 6/1984 |
| EP | 0180321 B1 | 2/1991 |
| EP | 0442224 A2 | 8/1991 |
| EP | 2390660 A1 | 11/2011 |
| WO | 2004070377 A2 | 8/2004 |
| WO | WO2006034182 A1 | 3/2006 |
| WO | 2008024500 A2 | 2/2008 |
| WO | WO2012074455 A1 | 6/2012 |

OTHER PUBLICATIONS

Srinivasan et a., "Suppressor Design and Detection for Ion Chromatography" in: "Applications of Ion Chromatography for Pharmaceutical and Biological Products," Mar. 9, 2012, John Wiley & Sons, Inc., pp. 91-105.
Dionex Column Product Manual for IonPac AS22 IonPac AS22-Fast, Doc No. 065119-08, Mar. 2013, 63 pages.
Dionex Column Product Manual for IonPac AS23, Doc No. 065120-06, May 2013, 51 pages.
Dionex Column Product Manual IonPac AS15, Document No. 031362-10, Jun. 2014, 60 pages.
Dionex Product Manual ASRS(R) 300 CSRS(R) 300, Document No. 031956, Rev. 05, Aug. 2007, 51 pages.
Dionex Product Manual for ERS 500 Suppressor, Doc No. 031956-09, Nov. 2013, 69 pages.
Dionex Product Manual for IonPac(R) CG12A IonPac(R) CS12A, Doc No. 031132, Rev. 09, May 2010, 78 pages.
Dionex Product Manual IonPac AS18 Fast, Document No. 031878-08, Jun. 2012, 54 pages.
Douglas et al., "New suppressor technology improve trace level anion analysis with carbonate-hydrogencarbonate mobile phases," J Chrom A, 956, 2002, 47-51.
Saari-Nordhaus et al., "Recent advances in ion chromatography suppressor improve anion separation and detection," J Chrom A, 956 (2002) 15-22.
U.S. Appl. No. 13/674,738, filed Nov. 12, 2012, to Srinivasan (specification, claims, abstract only).

* cited by examiner

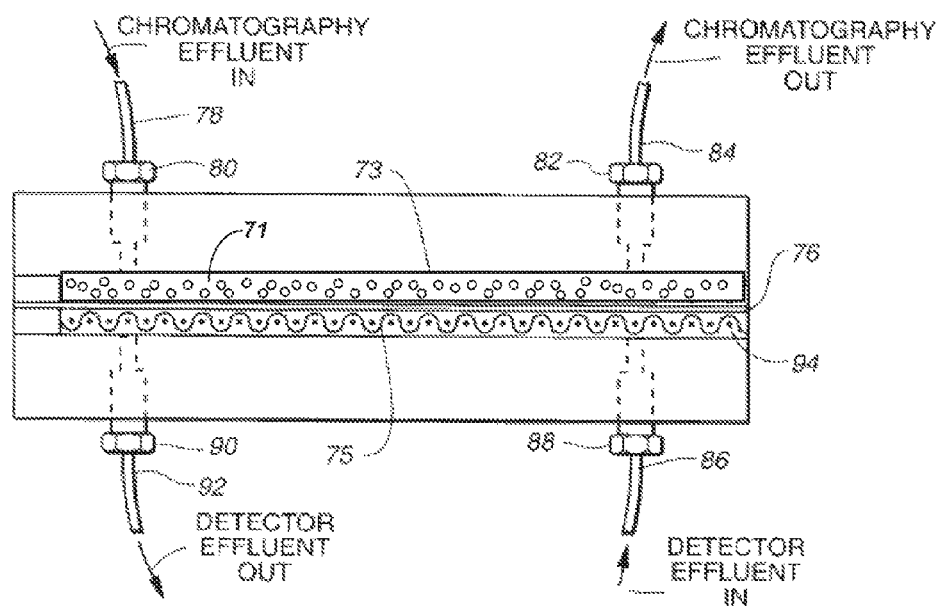
Figure 5
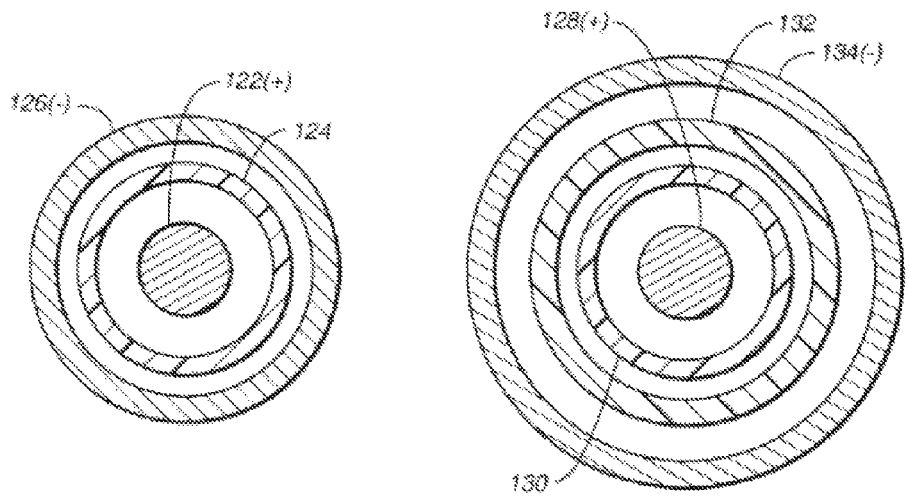
Figure 6
Figure 7

CURRENT EFFICIENT ELECTROLYTIC DEVICE AND METHOD

BACKGROUND OF THE INVENTION

One form of suppressor for ion chromatography is described in U.S. Pat. No. 4,999,098. The suppressor includes an ion receiving or regenerant channel and a sample stream or chromatographic effluent channel separated by an ion exchange membrane sheet. The sheet allows transmembrane passage of ions of the same charge as its exchangeable ions. Ion exchange screens are used in the channels. Flow from the sample flow channel is directed to a detector, such as an electrical conductivity detector, for detecting the resolved ionic species. The screens provide ion exchange sites and serve to provide site-to-site transfer paths across the sample flow channel so that suppression capacity is no longer limited by diffusion of ions in the bulk solution to the membrane. A sandwich suppressor is also disclosed including a second membrane sheet opposite to the first membrane sheet and defining a second channel. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the possibility of using water to replace the regenerant solution in the electrodialytic mode.

U.S. Pat. No. 5,248,426 discloses a suppressor of the general type described in U.S. Pat. No. 4,999,098 in an ion chromatography system in which the effluent from the detector is recycled to the flow channel(s) in the suppressor adjacent the sample stream flow channel.

U.S. Pat. No. 5,597,481 discloses a suppressor of the foregoing type used in sample pretreatment to reduce or suppress matrix ions in the eluent of opposite charge to the analyte ions and then to analyze the analytes in their conductive forms. Using existing suppressor devices, ion exchange interactions and hydrophobic interaction of the analyte, particularly in the eluent flow channel, affects recovery of certain analytes such as oligonucleotides and oligosaccharides.

In all of the disclosed approaches, currents higher than theoretically predicted are required for achieving quantitative suppression. Under high eluent concentration conditions, this high current translates into heat generation and high background noise.

U.S. Pat. No. 6,077,434 (the '434 patent) discloses improved suppressor current efficiency for an ion chromatography membrane suppressor. Current efficiency is disclosed to be inversely related to static capacity of the sample flow channel of the suppressor. Specifically, it teaches that a decrease in the static capacity in that channel results in an increase in current efficiency leading to maximum efficiency when the channel had no capacity, such as with a neutral screen in the channel. Current efficient suppressors have the benefits of low wattage, low level of leachates, lower noise and background and fast start up times. On the other hand, static capacity in the sample flow channel provides residual capacity for suppression that could be used, particularly when no current is applied to the suppressor. The higher static capacity is also useful during installation or startup of the device when the current to the suppressor device is turned off. This allows operation of the ion chromatograph without down time.

A benefit of high static capacity is when the suppressor is used in an intermittent mode of operation as discussed in U.S. Pat. No. 5,569,365 where the power is turned off for a set duration, e.g. during suppression and separation of analytes for detection. The key benefit of this mode is low noise. Under these conditions the static capacity is used to exchange the eluent and sample counter ions.

SUMMARY

One embodiment is an apparatus for treating an aqueous stream, said apparatus comprising a first ion exchange membrane having exchangeable ions of a first charge and capable of passing ions of said first charge, an aqueous stream flow channel having an inlet and an outlet, an ion receiving flow channel adjacent to said aqueous stream flow channel and separated therefrom by said first membrane, stationary flow-through ion exchange packing of the same charge as said ion exchange membrane disposed in said ion receiving flow channel, a packed bed of ion exchange particles disposed in and extending between said aqueous stream flow channel inlet and outlet, a portion of said packed bed being packed at a density less than 2 grams of packed dry particles per cc of the sample stream flow channel, said packed bed portion extending from said aqueous stream flow channel outlet upstream to at least 30% of the distance between said aqueous stream inlet and outlet, and first and second electrodes being in electrical communication with said aqueous stream flow channel and ion receiving flow channel, respectively.

Another embodiment is a method for treating an aqueous stream including matrix ions using an apparatus of the foregoing type. The method comprises flowing the aqueous stream through the aqueous stream flow channel; simultaneously flowing an ion receiving stream through first ion receiving flow channel to remove at least a portion of said matrix ions from said aqueous stream. A specific method is one in which the aqueous stream is a sample stream including analyte ions and in which the matrix ions are suppressed and the ion exchange membrane is regenerated.

BRIEF DESCRIPTION OF THE DRAWINGS

FIGS. 4 and 5 are an exploded view of a one membrane suppressor according to the invention.

FIGS. 6 and 7 are schematic cross-sectional views of tubular forms of suppressor according to the invention.

Like reference numerals refer to corresponding parts throughout the several views of the drawings.

DETAILED DESCRIPTION OF EMBODIMENTS

Figure 1:
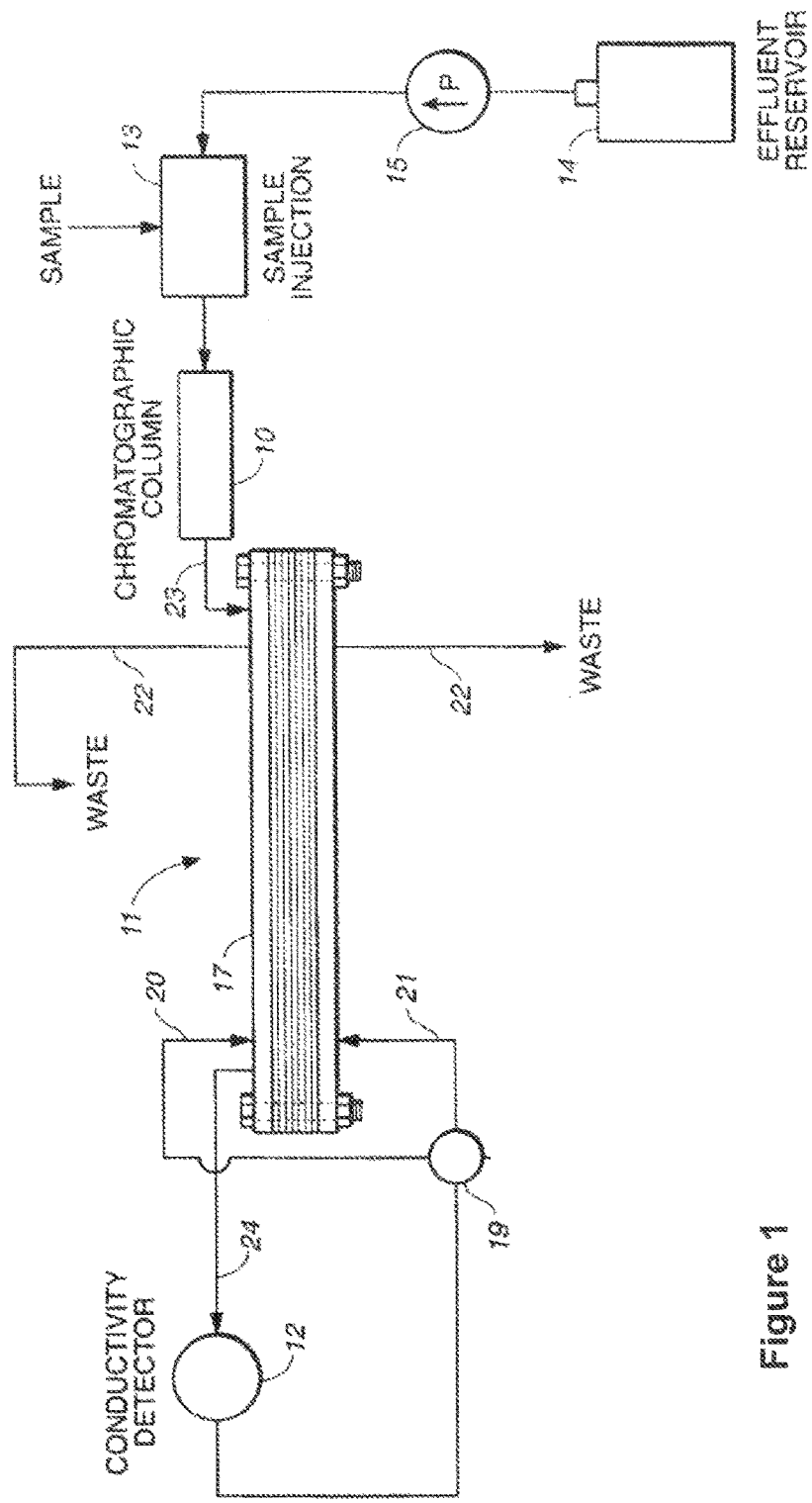
FIG. 1 is a schematic view of apparatus for performing chromatography using a suppressor according to the invention.

The system of the present invention is useful for determining a large number of anions or cations. Suitable samples include surface waters and other liquids such as industrial chemical waste, body fluids, and beverages such as fruits, wines and drinking water. It is also useful for purifying a water or eluent stream, such as one used for chromatography, or as a pH modifier.

In one embodiment, the present invention is directed to a method and apparatus for treating an aqueous sample stream including analyte ions of one charge and matrix ions of opposite charge. In one application, the treatment is in a suppressor for ion chromatography and the matrix ions are the electrolyte ions in the eluent of opposite charge to the analyte ions. In another application, the method and apparatus is used for pretreating an aqueous sample stream prior to analysis, preferably including separation on a chromatography column. In this instance, the matrix ions typically are compounds of high ionic strength in the sample stream (e.g., commercial sodium hydroxide) which can obscure the sample peaks by large interfering peaks of the sample matrix ions. Such matrix ions can severely change chromatography because the sample matrix ion is of such high concentration it becomes the major eluting ion, temporarily overriding the eluent. A typical minimum concentration to warrant pretreatment is when the matrix ion is at least ten times the molar ionic concentration of the chromatographic eluent. Such a system to which the present improvement in current efficiencies is applicable is set forth in Stillian, et al., U.S. Pat. No. 5,597,481, incorporated herein by reference.

As used herein, the term "matrix ion" refers to either the electrolyte in an eluent used for chromatography which is suppressed or whose concentration is reduced to non-interfering levels after separation and prior to detection, or to matrix ions in a sample stream whose concentration is significantly reduced prior to separation and/or detection. Since, in either case, the matrix ions are suppressed in the device, the term "suppressor" will be used generically to include a suppressor for ion chromatography and a pretreatment device including the modifications of the present invention.

For the analysis of anions, the matrix ions typically are a base (e.g., sodium hydroxide or other alkyl metal hydroxides). Other matrix compounds include sodium carbonate, ammonium hydroxide, or over alkyl ammonium hydroxide. For cation analysis, the matrix ions typically are an acid such as a common mineral or organic acid (e.g., sulfuric acid, phosphoric acid or methane sulfonic acid).

During suppression, the conductivity and noise caused by matrix ions in an analysis stream is reduced. The present invention serves to increase the current efficiency of the suppressors described above. Various embodiments of such current efficient suppressors will be described herein.

In one embodiment, a suppressor of increased current efficiency will be described with respect to a chromatography system of the type using an electrochemical suppressor with detector effluent recycle as shown in Stillian, et al., U.S. Pat. No. 6,077,434, incorporated herein by reference.

The specific purpose of the suppressor stage in ion chromatography is to reduce the conductivity and noise of the analysis stream background while enhancing the conductivity of the analytes (i.e., increasing the signal/noise ratio), while maintaining chromatographic efficiency. Thus, the following parameters bear upon the performance of the suppressor: (1) dynamic capacity of suppression, measured as µEq./min of eluent for each device with the power on (i.e., voltage or current is applied to the electrodes of the suppressor); and (2) background conductivity of the effluent exiting the sample flow channel that is measured as µS/cm per device.

Referring to FIG. 1, a simplified schematic apparatus for performing the present invention is illustrated using a recycle stream from the detector to the suppressor. The system includes a chromatographic separator, typically in the form of a chromatographic column 10 which is packed with a chromatographic separation medium. In one embodiment referred to above, such medium is in the form of ion-exchange resin. In another embodiment, the separation medium is a porous hydrophobic chromatographic resin with essentially no permanently attached ion-exchange sites. This other system is used for mobile phase ion chromatography (MPIC) as described in U.S. Pat. No. 4,265,634. An ion exchange site-forming compound, including hydrophobic portion and an ion-exchange site, is passed through the column and is reversibly adsorbed to the resin to create ion-exchange sites.

Arranged in series with column 10 is a suppressor 11 serving to suppress the conductivity of the electrolyte of the eluent from column 10 but not the conductivity of the separated ions. The conductivity of the separated ions is usually enhanced in the suppression process.

The effluent from suppressor 11 is directed to a detector, preferably in the form of flow-through conductivity cell 12, for detecting all the resolved ionic species therefrom. A suitable sample is supplied through sample injection valve 13 which is passed through the apparatus in the solution of eluent from eluent source or reservoir 14 drawn by pump 15, and then passed through the sample injection valve 13. The chromatography effluent solution leaving column 10 is directed to suppressor 11 wherein the electrolyte is converted to a weakly conducting form. The chromatography effluent with separated ionic species is then treated by suppressor 11 and passed through conductivity cell 12.

In conductivity cell 12, the presence of ionic species produces an electrical signal proportional to the amount of ionic material. Such signal is typically directed from the cell 12 to a conductivity meter, not shown, thus permitting detection of the concentration of separated ionic species.

The effluent from conductivity cell 12, referred to herein as the detector effluent, is directed to at least one flow-through detector effluent channel in ion-exchange membrane device 17. The membrane device will be described in detail hereinafter. As illustrated, the detector effluent flows through a splitter valve or tee 19 which separates the detector effluent into two different conduits 20 and 21 to supply the detector effluent to flow-through channels on opposite sides of the two membranes of the suppressor adjacent the central sample stream flow channel and then to waste through conduit 22. In one alternative, the detector effluent flows through such channels sequentially and then to waste. The chromatography effluent flows from chromatographic column 10 to membrane device 17 through conduit 23, and from the membrane device to the conductivity detector through conduit 24.

Sandwich Suppressor Device.

Figure 2:
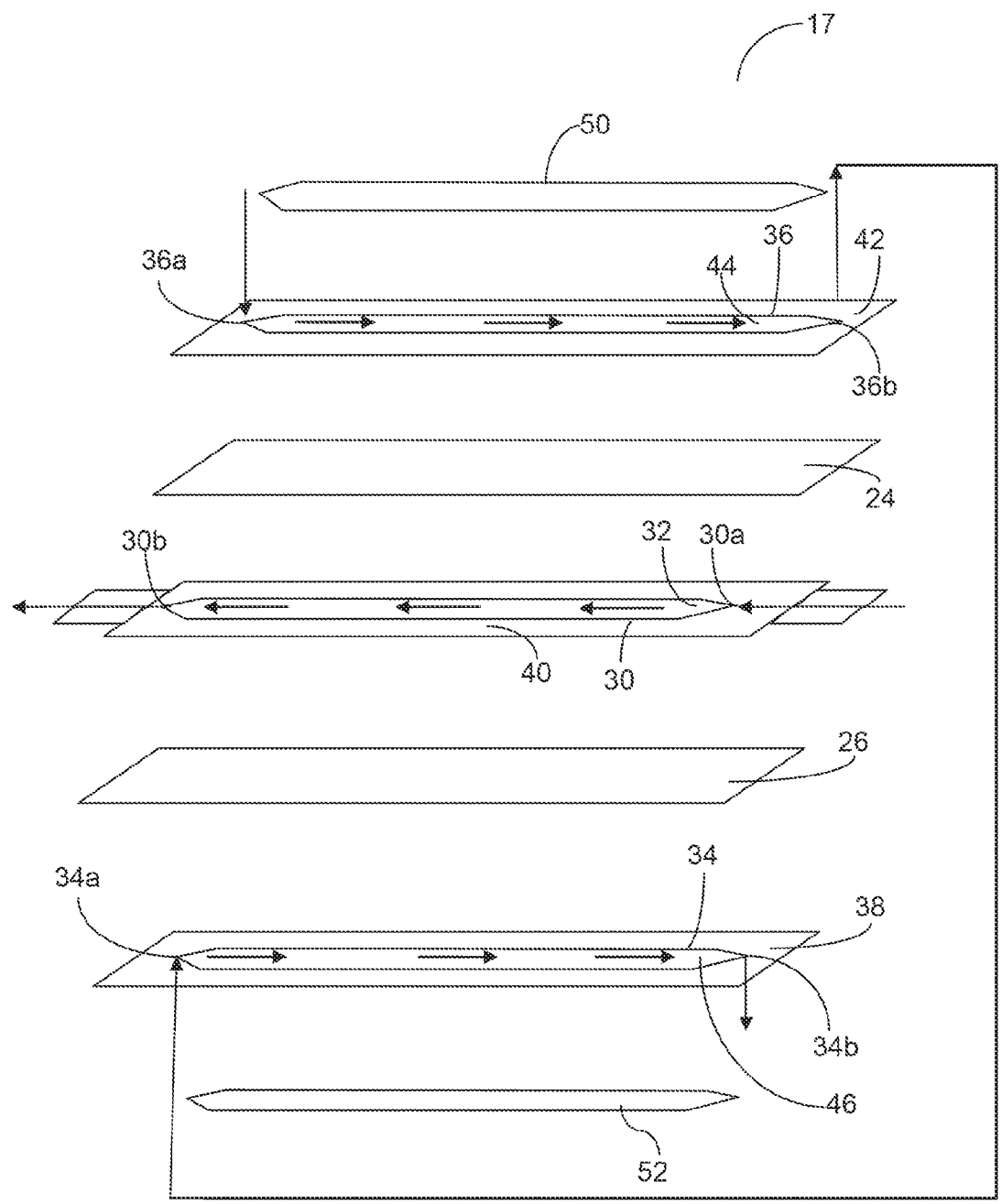
FIG. 2 is an exploded schematic view of a sandwich membrane suppressor according to the invention.

Referring to FIG. 2, the sandwich-type membrane suppressor 17 of FIG. 1 is illustrated in schematic form as one embodiment of the invention. It may be of the type illustrated and described with respect to the membrane suppressor of FIGS. 2-5 of U.S. Pat. No. 6,077,434, incorporated by reference, except for the packing in the central sample stream flow channel which will be described in detail hereinafter. Referring specifically to FIG. 2 herein, suppressor 17 includes a central sample stream flow channel or compartment 30 packed with a bed 32 of loosely packed ion exchange particles, to be described, flanked by an ion receiving flow channel 34 and an ion source flow channel 36. Ion exchange membrane sheets 26 and 24, suitably of the type described in the '434 patent, are mounted to extend along opposite sides of sample flow channel 30. Flow channels 30, 34, and 36 are defined by gaskets 40, 38, and 42, and by membranes 26 and 24, respectively. Charged ionic screens 44 and 46 are disposed in channels 36 and 34, respectively. Spaced electrodes 50 and 52 in the form of flat plate electrodes extend substantially along and across the length and width of channels 34 and 36, respectively, in electrical communication therewith.

A suitable alternative embodiment to the gasket configuration of FIG. 2, not shown, is illustrated in U.S. patent application Ser. No. 13/674,738, filed Nov. 12, 2012, incorporated herein by reference.

As illustrated, regenerant solution flows into inlet 36a of channel 36, out outlet 36b to inlet 34a of channel 34 and out outlet 34b. Sample ionic species in eluent flows in inlet 30a of channel 30 and out outlet 30b.

In one mode of operation of the suppressor device 17, effluent from chromatographic column 10 is directed through sample stream flow channel 30 bound by ion-exchange membranes 26 and 24 partitioning the detector effluent in channels 34 and 36 from the chromatography effluent in channel 30. The detector effluent flows from the conductivity cell through channels 34 and 36. The membranes are preferentially permeable to ions of the same charge as the exchangeable ions of the membranes and resist permeation of ions of opposite charge. The exchangeable ions of the membranes are in the ion form necessary to convert the developing reagent of the eluent to a weakly ionized form. For maximum capacity, the detector effluent flow is countercurrent to the sample stream flow. The chromatography effluent from chromatographic column 10 is passed through the sample stream flow channel and contacts both membranes. The membranes are simultaneously contacted on their outer sides with the detector effluent flowing in the opposite direction through in channels 34 and 36 so that membranes form a selective permeability partitions between the detector effluent and the sample stream from the chromatography column. Ions extracted from the same stream at the active ion-exchange sites of the membranes are diffused through the membranes and are exchanged with electrolytically generated ions, and thus diffuse ultimately into the detector effluent. Application of a potential across the electrodes increases the mobility of the ions across the membrane. The resolved ionic species in the effluent leaving the suppressor device are detected, as with a conductivity detector.

A significant difference between the sandwich suppressor described in the '434 patent and that of the present invention is the form of packing in sample flow channel 30. The '434 patent describes a charged screen form of packing and generally suggests that ion exchange particles may be packed in a bed in the channel instead. There is no disclosure of the form of the packed bed.

According to the invention, the packed bed of sample stream flow channel 30 is "loosely packed" at least in a region toward the exit end of channel 30. Such loose packing is defined by a density of less than 2 grams of packed dry particles in the bed per cubic centimeter (cc) of the sample stream flow channel, preferably less than 1.5 grams/cc of the sample stream flow channel, and most preferably less than 1 grams/cc of the sample stream flow channel. The packed bed preferably extends from the inlet to the outlet of channel 30. The loosely packed region extends from the sample stream outlet upstream to at least 30%, 40%, 50%, 60%, 70%, 80%, 90% to as much as 100%, of the distance between the sample stream channel inlet and outlet. To calculate density, the term "dry particles" distinguishes from the sticky swollen state of the particles when in contact with liquid in the channel. Dry particles are defined to have a moisture content of less than about 20%. To calculate the density of particles swollen as in aqueous liquid in the sample flow channel, the swollen particles are removed from the channel and dried to that moisture content to yield the dry particle weight prior to calculating density. Thus, the term "dry particles" refers to the weight of the particles when in a dry state, but the density is not limited to the packing of dry particles. For example, the term encompasses packing the particles in a slurry form into the channel.

The electrical conductivity through the loosely packed particles in channel 30 between the membranes is discontinuous, i.e. current is not freely transported between the particles since the particle density is not high enough to permit transport of current via transport of ions across the particles. This configuration results in less wastage current since there is essentially no continuous transport pathway from one particle bead to another between the walls of the sample flow channel transverse to flow. In contrast, if the packing was densely packed, the bead to bead distance is minimized causing the main current pathway to be from ion exchange through the beads. In the suppressor for anion analysis, the particles used are cation exchange beads that would permit the transport of electrolytically generated hydronium ions which would be transported to the cathode by the applied potential. In the present invention since the packing density is low, bead to bead transport of the current via ionic transport is minimized. This means the hydronium generated at the anode electrode is not easily transported across to the cathode thereby minimizing wastage current and improving current efficiency.

Preferably the ion exchange particles in bed 32 are high capacity ion exchange resin beads as that term is used in chromatography or other high capacity ion exchange particles. High capacity of the ion exchange resin is defined to be at least 0.3 milliequivalents/milliliters (meqv/mL), preferably at least 0.7 meqv/mL, more preferably at least 1.0 meqv/mL, and most preferably at least 1.5 meqv/mL. Suitable cation exchange resin is of the type 50W-X8 resin, 8% crosslinked (Polystyrene-divinylbenzene sulfonic acid resin, Particle diameter 63-150 μm) sold by Bio-Rad, Hercules, Calif., USA or Dowex 50 W-X8 resin, (Diethenyl-benzene polymer with ethenylbenzene and ethenylethylbenzene, sulfonated) 200-400 mesh sold by Sigma-Aldrich Corp., St. Louis, Mo., USA and suitable anion exchange resin is of the type AG1 resin, 8% crosslink (Polystyrene-divinylbenzene quaternary ammonium resin, Particle diameter 45-106 μm) sold by Bio-Rad, Hercules, Calif., USA. A suitable size range for the ion exchange resin is 1 to 200 μm more preferably 5 to 30 μm, and most preferably 20 to 60 μm. A suitable crosslinking range for the ion exchange resin is in the 2 to 55% regime, preferably in the 8 to 16% regime.

The static capacity of the packed bed in channel 30 and adjacent one or two membranes may be at least 3 meqv/mL of the sample flow channel volume, preferably at least 5 meqv/mL, and most preferably at least 7 meqv/mL of the sample flow channel volume. Such static capacity is measured by pursuing a breakthrough capacity measurement of the suppressor by pumping a known concentration of an eluent at a known flow rate but by keeping the power to the suppressor off. The static capacity is thus the ion exchange capacity of the suppressor when the device power is off (as opposed to the dynamic capacity of the suppressor when the device power is on) to electrolytically regenerate the ion exchange material. The static capacity refers to the available ion exchange capacity intrinsic to the ion exchange packing and the ion exchange membrane in the sample stream flow channel.

One way of determining the static capacity is by monitoring the effluent from the suppressor eluent channel using conductivity detection. For example, when pursuing anion analysis with base eluents, the base can be pumped at a known concentration and flow rate and the effluent conductivity is monitored. Initially, since the base would be suppressed to water the conductivity will be low. Once the capacity of the suppressor is exhausted the base would no longer be exchanged and would be detected in the detector as a rising conductivity. The time required for this breakthrough of base to occur multiplied by the product of concentration and flow rate (equivalents of the eluent ml/min.) provides the static capacity of the suppressor device in meqv. The static capacity when divided by the volume of the suppressor sample flow channel between the inlet and the outlet (excluding the packing) provides the static capacity of the device in meqv/mL of the sample flow channel. The volume of the suppressor sample flow channel can be estimated by measuring the dimensions or by measuring the retention time of an analyte peak with and without the device installed.

The loosely packed ion exchange particles in the sample flow channel may be packed dry or premixed with water as in a slurry for packing. In the simplest case, for resin particles, the sample flow channel may be packed by placing the known quantity of the resin in dry form into the sample flow channel using a spatula. The dry resin particles can be spread out evenly in the channel before assembling the device. The resin particles can be in the salt form (e.g., sodium form) for cation exchange resin particles or methane sulfonic acid form for anion exchange resin particles or can be in the regenerated form (hydronium form for cation exchange resins or hydroxide form for anion exchange resin particles). Alternatively, the resin particles can be placed in a slurry of suitable aqueous solution and then packed into the sample flow channel by using a packing pump. In this case the resin particles are packed into the sample flow channel by positive displacement. Alternatively, a vacuum can be used to pack the resin particles in the sample flow channel. In this case, the vacuum is applied to the sample flow channel outlet while the sample flow channel inlet is in contact with the resin particle slurry.

Typically, the channel would develop some inherent pressure drop due to the packing material. A suitable pressure drop from the inlet to the outlet of the sample flow channel is less than 500, 300, 200, 150, 100, or 50 psi, preferably between 20 and 300 psi more preferably between 50 to 150 psi and most preferably between about 80 to 120 psi. Pressure can be measured by using a pressure transducer.

The use of the loosely packed ion exchange particle results in high current efficiency defined by the minimum current required to suppress a given eluent strength. This current is then compared to the theoretical current obtained by Faraday's law for a given eluent strength. U.S. Pat. No. 7,399,415 column 6 and U.S. Pat. No. 6,077,434 describe the methodology to measure the current efficiency. 100% Faradaic efficiency can be calculated using Equation 1, as follows:

$$I_{100} = FCV/60$$

where $I_{100}$% is the current in mA for a 100% current efficient device, F is Faraday's constant (coulombs/equiv), C is the concentration (of the suppressed anions or cations in M, and V is the flow rate in ml/minute. % Current efficiency (% CE) can be calculated using Equation 2, as follows:

$$I_{min} = (T_{100}\% * 100)/(\% \text{ CE})$$

where $I_{min}$ is the minimum current required for a given current efficiency, and % CE is the current efficiency expressed as a %. Preferably, the current efficiency is at least 75%, and more preferably is at least 80%, 85%, 90%, or 95% and most preferably is about 100%.

It is believed that the high current efficiency is achieved using the loosely packed high capacity ion exchange bed because it results in a relatively resistive pathway in the sample flow channel. There is poor bead to bead contact, and so that the resistance in the eluent channel is high. It is believed that this configuration forces the current to be mainly carried by the eluent in the channel and results in high current efficiency. There is no substantial transport of species in forming wastage current. The net effect of this configuration is the dual benefit of high static capacity of the suppressor with excellent current efficiency.

The loosely packed bed of the invention is particularly effective in the intermittent mode of suppressor operation as disclosed in U.S. Pat. No. 5,569,365 in which the suppressor current can be turned off during the suppression, and/or detection but not during regeneration of the ion exchange membranes. The mode of intermittent operation of this patent is incorporated by reference except for the use of the loosely packed bed of ion exchange particles in the sample flow channel disclosed herein. There, high static capacity combined with high current efficiency is preferred since the high current efficiency would ensure good regeneration to occur at a fast pace. In the intermittent mode the time of regeneration is added to the overall run time therefore having high current efficiency is beneficial to the overall run time. Under these conditions, ion exchange occurs on all available ion exchange functionalities. There is no directionality to the exchange process for suppression. In contrast if a small current is applied during suppression according to the present invention the electrical potential generated would ensure directionality, and the ions would be removed albeit slowly in the direction of the field for example cations would be removed in the direction of the cathode. Another benefit of applying a small current, e.g. 1 to 5 mA, is lower baseline drift. In contrast, prior art suppressor devices that were used for the intermittent mode of operation had poor current efficiency therefore required significant time for regeneration. In other words the run time was longer with prior art suppressor devices in the intermittent mode of operation. With the devices of the present invention the limitation of the prior art suppressors are overcome and it is feasible to achieve short run times with current efficient suppressor devices. For example, a prior art device that is 50% efficient would require two times as long to electrolytically regenerate as a suppressor device that is 100% current efficient for the same applied current.

Figure 3:
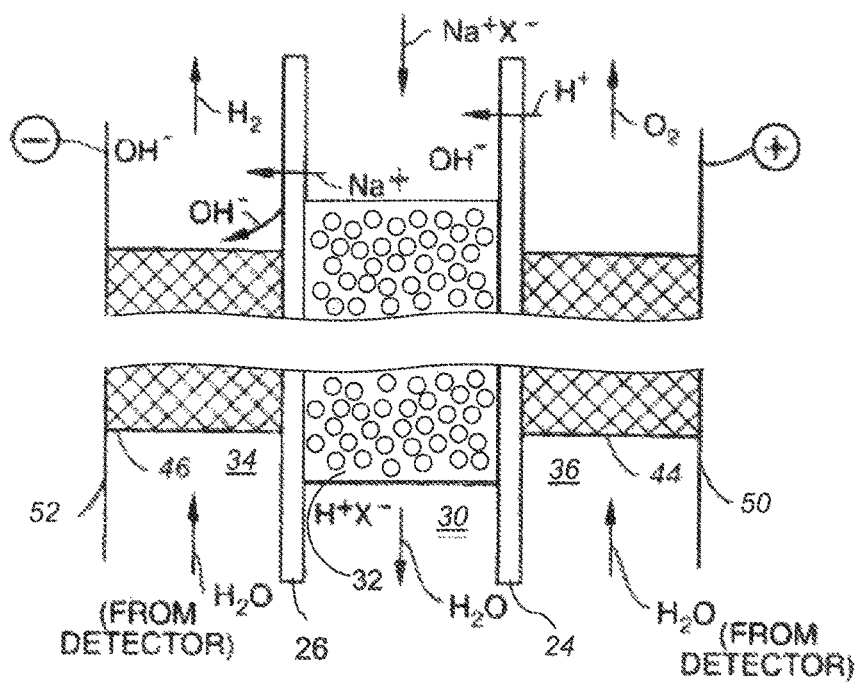
FIG. 3 is a schematic expanded view of the suppressor of FIG. 2 showing simplified ion transfer.

FIG. 3 schematically illustrates the electrochemical operation of the present invention for a particular system, using a sandwich suppressor with screens 44 and 46 in flow channels 36 and 34, respectively, and the loosely packed ion exchange particle bed 32 in channel 30 in which an electrical potential is applied between spaced electrodes. The system illustrated is for anion analysis and includes sodium hydroxide as the electrolyte of the effluent to be converted into weakly ionized form ($H_2O$) in the suppressor. Thereafter, the solution passes through the conductivity cell and is recycled to flow channels 34 and 36. The ion-exchange membrane sheets allow the positively charged sodium and hydronium ions to permeate across the membrane together.

In the illustrated embodiment of FIG. 3 for anion analysis, the positively charged sodium ions of the electrolyte in channel 30 electromigrate under the influence of the electric field, across the negatively charged membrane 26 into channel 34. The hydronium ions generated at the anode 50 by electrolysis of water, flow from channel 36 across membrane 24 into channel 30 to form water with hydroxide ions therein. The sodium ions, being attracted to the negative electrode, are more rapidly removed leading to a substantial increase in the capacity of the suppressor device.

Figure 4:
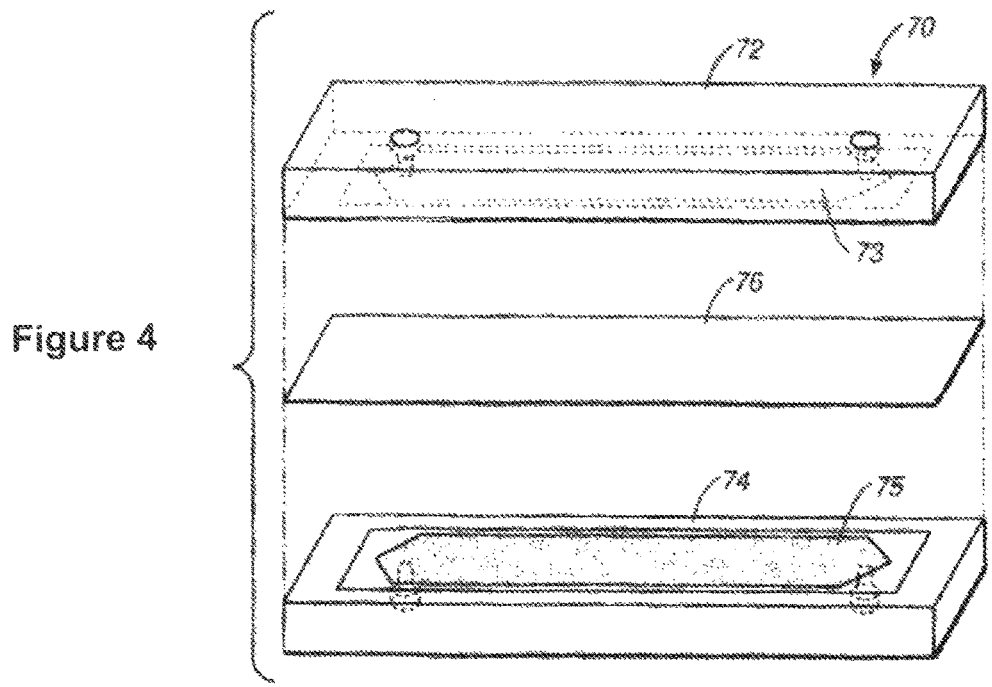

Referring to FIGS. 4 and 5, another embodiment of suppressor 70 is illustrated using a single membrane. Suppressor 70 includes upper rigid support block 72 with sample stream flow channel wall 73 and lower support block 74 with ion receiving flow channel wall 75, separated by an ion-exchange membrane 76 of the type described above.

The chromatography effluent flows into the suppressor device through effluent inlet 78, fitting 80 and flows along a sample stream flow channel defined by wall 73, through a bed of loosely packed ion exchange particles 71 and then through fitting 82 and out sample stream outlet line 84. Similarly, detector effluent solution flows from inlet line 86 through fitting 88 across the ion receiving flow channel defined by wall 75, through screen 94, out fitting 90 and through ion receiving flow channel outlet 92 to waste. Referring to FIG. 5, it should be noted that a first electrode is disposed in the ion receiving flow channel 75 and a second electrode is disposed in the sample stream flow channel.

The liquid flows through the channels formed by the spacing among the projections. The dimensions of the projections and spacing are selected to provide the desired frequency of contacts with the flowing ions to increase their mobility across the membrane and to create sufficient turbulence for increased mixing efficiency.

Suitable eluent solutions for ion chromatography of anions include alkali hydroxides, such as sodium hydroxide, alkali carbonates and bicarbonates, such as sodium carbonate, alkali borates, such as sodium borate, combinations of the above, and the eluent systems of the aforementioned patents.

The system of the present invention is also applicable to the analysis of cations (e.g., lithium, sodium, ammonium, potassium, magnesium, and calcium). In this instance, the electrolyte of the eluent is typically an acid which does not damage the membrane. Methane sulfonic acid has been found to be inert to the membrane under electrolytic conditions. Other acids such as nitric acid and hydrochloric acid produce electrochemical by-products that may damage the membrane and are, thus, not generally preferred for that typical membrane.

In cation analysis, the flow of the electrolyte ion is from the cathode toward the anode, rather than the reverse as in anion analysis and the ion exchange screens and membranes are aminated and permeable to anions. Thus, in the negatively charged ion source flow channel, water is converted to hydroxide ion and hydrogen gas. The hydroxide ion passes through the adjacent membrane into the sample stream flow channel and combines with hydrogen ion (or an amine or other basic organic molecule group) to form weakly ionized electrolyte. The negatively-charged transmembrane ion travels through the second membrane into the positively-charged ion receiving flow channel under influence of the anode to form an acid which passes to waste. In summary, for cation analysis, the electrical charges of the analyte, eluent reagent, and membranes are reversed with respect to anion analysis.

Referring to FIG. 6, a schematic cross-sectional view of a tubular form of the electrodialytic suppressor of the present invention is illustrated. In this instance, it is assumed that the sample stream flow channel is the lumen of the innermost tube. The device includes anode 122 (in the form of a rod or wire, e.g., formed of platinum, gold, carbon or stainless steel), cation exchange membrane 124, and outer wall 126, which may be formed of a conductive material to serve as the cathode. In one embodiment, high capacity flow-through ion exchange packing in the form of a bed of ion exchange resin particles is disposed in the ion receiving flow channel and the loosely packed bed of high capacity ion exchange particles of the present invention is disposed in the sample stream flow channel. This system is comparable in general function to the one illustrated in FIG. 2. Alternatively, the ion receiving flow channel may be the lumen of the inner tube. In this instance, the polarities of the electrodes are reversed. Membrane 124 may be formed of stretched or unstretched tubular ion exchange membranes, e.g., Nafion 811X from Perma-Pure Products, J.S. Outer wall 126 may be formed of an 18 gauge stainless steel (SS) tubular case.

FIG. 7 illustrates a tubular type of dual-membrane suppressor of similar function to the sandwich membrane suppressor. It is generally constructed by inserting a length of suitably inert wire inner electrode 128 into a length of tubular inner membrane 130 which is itself inserted inside a length of somewhat larger diameter tubular outer membrane 132 and enclosing the whole assembly in stainless steel tube 134 of appropriate dimensions. The outer tube itself functions as the electrode, connections being made at the ends to allow access to the flow channels between the inner electrode and inner membrane, between the two membranes (annulus) and between the outer membrane and stainless steel case. High capacity flow through ion exchange packing in the form of a bed of ion exchange resin particles is disposed in the ion receiving flow channel with neutral or low capacity or open space in the sample stream channel.

The invention has been described with respect to a suppressor and its method of use for suppression in ion chromatography. However, it is also applicable to the use of an electrolytic device in which loosely packed ion exchange particles are packed in one channel of the device. For example, it is applicable to devices for treating aqueous streams including matrix ions to be removed but where the aqueous stream does not include analyte ions. A specific application of such a device is an electrolytic purifier, e.g. one for purifying water or an eluent, such as one used to carry analyte ions through a chromatography column. It is also applicable to a pH modifier in which matrix ions are removed from the aqueous stream flow channel.

The structure of the purifier device or pH modifier may be the same as the suppressor described above. For the purifier, the aqueous sample stream to be treated includes matrix ions to be removed during purification, in a manner similar to suppression described above. Thus, during purification the matrix ions are transported from the aqueous flow channel through the ion exchange membrane to the ion receiving flow channel. The parameters of the suppressor device and method are applicable to such purifier devices. The principal difference in the method is that the aqueous stream is not a sample stream and so does not include analyte ions to be detected. Here the ion receiving flow channel has an upstream portion containing the matrix ions and a downstream portion in which the matrix ions have been at least partially removed.

In order to illustrate the present invention, the following non-limiting examples of its practice are provided.

EXAMPLES

Example 1

A 4 mm anion self-regenerating suppressor (ASRS) was assembled and plumbed following the schematic of FIG. 2. A polystyrene divinyl benzene based sulfonated cation exchange resin that had 16% crosslinking was used. The capacity of this resin was 2.0 meqv/mL. Approximately 0.4 g of the resin was placed along the total length of the eluent sample stream channel in a dry form to provide a density of 1.62 grams/cc. Cationic ion exchange screens were placed in the regenerant channels. Once the device was assembled and the device was hydrated it was ready for use. The static capacity was measured and was roughly 2.0 meqv for the eluent channel that included the exchange capacity of the ion exchange membranes and the ion exchange resin. The static capacity calculated was 7.4 meqv/mL of the sample stream flow channel. The static capacity of a standard commercial suppressor sold under the name 4 mm ASRS 300 was roughly 270 µeqv. The static capacity calculated was approximately 1.0 meqv/mL of the sample stream flow channel of the standard commercial suppressor. The device of the present invention had roughly a greater than 7 fold higher capacity than the prior art. The device was used as a suppressor for anion analysis using an IonPac AS15 (4×250 mm) column from Thermo Fisher Scientific. The eluent used was 38 mM KOH which was generated by an eluent generator module. The flow rate was 1.2 ml/min. The recommended current as per Chromeleon chromatography data system software (Thermo Fisher Scientific, Inc.) recommendations was 113 mA, which was optimal for the ASRS 300 suppressor. The suppressor was also tested at lower currents and ran overnight for several runs to ensure that the current was sufficient for suppression. The suppressor was able to suppress the eluent at a current efficiency of 94% with a current of 78 mA. The performance of the suppressor response at the recommended current setting of 113 mA (3.5 V) and the setting of 78 mA (3.3 V) is shown in Table 1. These results illustrate that the suppressor is providing consistent response and is highly current efficient as evident from complete suppression at a current setting of 78 mA which is calculated as 94% current efficiency. The static capacity of the device is also significant when compared to the ASRS 300 suppressor of the prior art. The device of the present invention also showed a 35% lower wattage than the recommended setting illustrating the benefit of operating the device at the current efficient regime.

TABLE 1

Peak response at two current settings with the suppressor device of the present invention.
Peak Response (Area units)

| | Current Setting | 113 mA | 78 mA |
|---|---|---|---|
| 1 | Fluoride | 1.0641 | 1.0865 |
| 2 | Chloride | 3.1023 | 3.1811 |
| 3 | Nitrite | 2.1218 | 2.3224 |
| 4 | Sulfate | 2.3021 | 2.3586 |
| 5 | Bromide | 1.3244 | 1.3580 |

TABLE 1-continued

Peak response at two current settings with the suppressor device of the present invention.
Peak Response (Area units)

| | Current Setting | 113 mA | 78 mA |
|---|---|---|---|
| 6 | Nitrate | 1.7164 | 1.7672 |
| 7 | Phosphate | 2.0035 | 2.0231 |

Figure 8A:
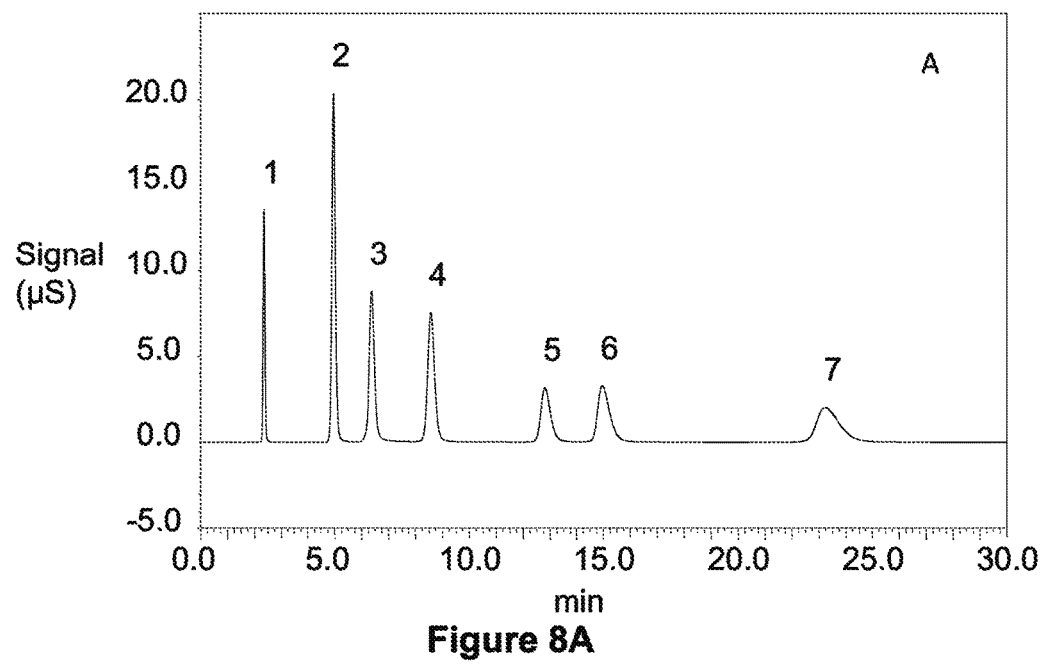
FIGS. 8A,B-11A,B are chromatograms illustrating use of the present invention.
Figure 8B:
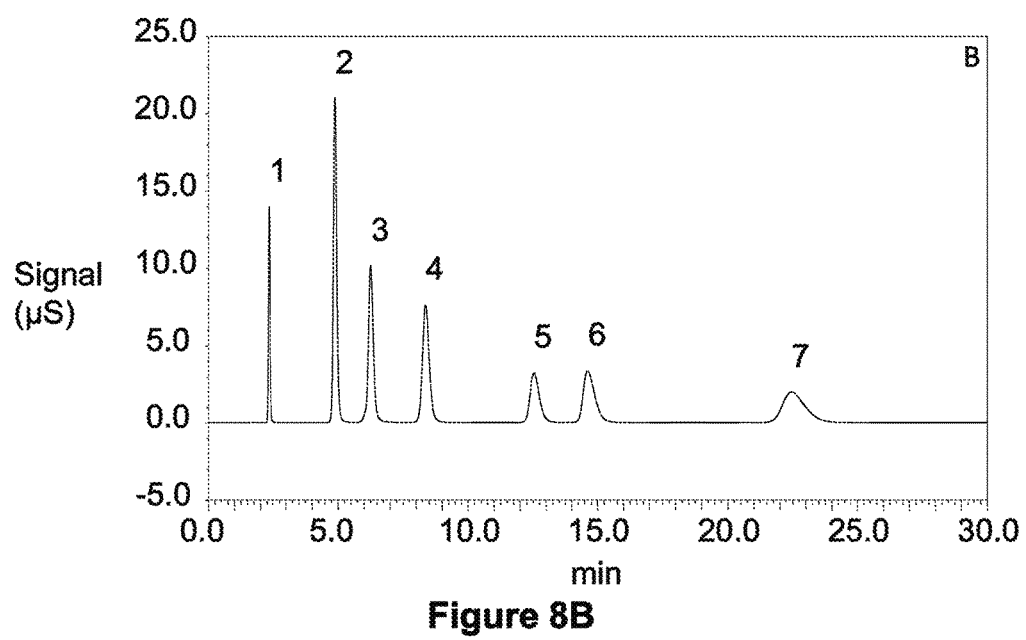

FIG. 8 shows separation of a test mixture of seven anions is shown above using a current setting of 113 mA (A) and 78 mA (B) using the suppressor device of the present invention.

Example 2

A 2 mm ASRS suppressor was assembled and plumbed following the schematic of FIG. 2. The cation exchange resin from example 1 was used in this example. Approximately 0.08 g of dry resin was placed along the length in the eluent channel in a dry form. Cationic ion exchange screens were placed in the regenerant channels. Once the device was assembled and the device was hydrated it was ready for use. The static capacity was measured and was roughly 0.4 meqv for the eluent channel that included the exchange capacity of the ion exchange membranes and the ion exchange resin. The static capacity calculated was 6.84 meqv/mL of the sample stream flow channel. The static capacity of a standard commercial suppressor sold under the name 2 mm ASRS 300 was roughly 55 µeqv. The device of the present invention had roughly a greater than 7 fold higher capacity than the prior art. The static capacity calculated for the commercial device was 0.81 meqv/mL of the sample stream flow channel. The device was used as a suppressor for anion analysis using an IonPac AS15 (2×250 mm) column from Thermo Fisher Scientific. The eluent used was 38 mM KOH which was generated by an eluent generator module. The flow rate was 0.3 ml/min. The recommended current as per Chromeleon recommendations was 29 mA which was optimal for the ASRS 300 suppressor. The suppressor was also tested at higher currents and ran overnight for several runs to ensure that the current was sufficient for suppression. The suppressor was able to suppress the eluent at a current efficiency of 85% with a current of 21 mA. The performance of the suppressor response at the recommended current setting of 29 mA (3.87 V) and the setting of 21 mA (3.73 V) is shown in Table 2. These results illustrate that the suppressor is providing consistent response and is highly current efficient as evident from complete suppression at a current setting of 21 mA which is calculated as 85% current efficiency. The static capacity of the device is also significant when compared to the ASRS 300 suppressor of the prior art. The device of the present invention also showed a 31% lower wattage than the recommended setting illustrating the benefit of operating the device at the current efficient regime. Note that the wattage of a suppressor is proportional to $I^2R$ where I=the applied current and R=the resistance of the sample flow channel.

TABLE 2

Peak response at two current settings with the suppressor device of the present invention.
Peak Response (Area units)

| | Current Setting | 29 mA | 21 mA |
|---|---|---|---|
| 1 | Fluoride | 0.8950 | 0.8844 |
| 2 | Chloride | 2.6200 | 2.5932 |
| 3 | Nitrite | 1.5513 | 1.7514 |
| 4 | Sulfate | 1.9466 | 1.9748 |
| 5 | Bromide | 1.0955 | 1.0963 |
| 6 | Nitrate | 1.4760 | 1.4870 |
| 7 | Phosphate | 1.5355 | 1.5632 |

Figure 9A:
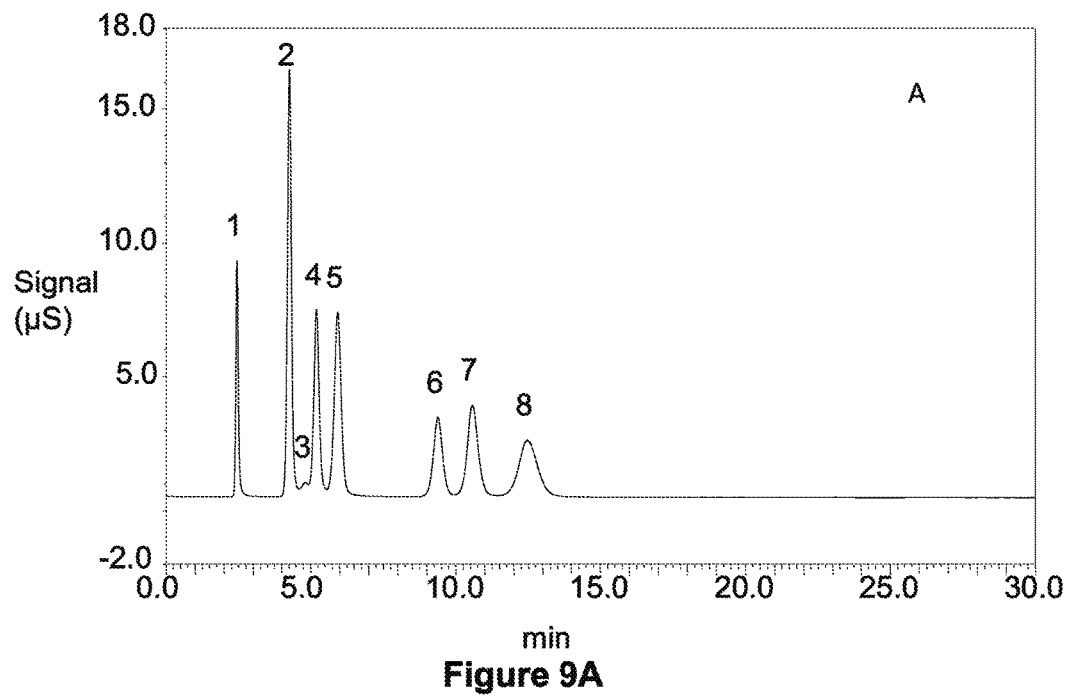
Figure 9B:
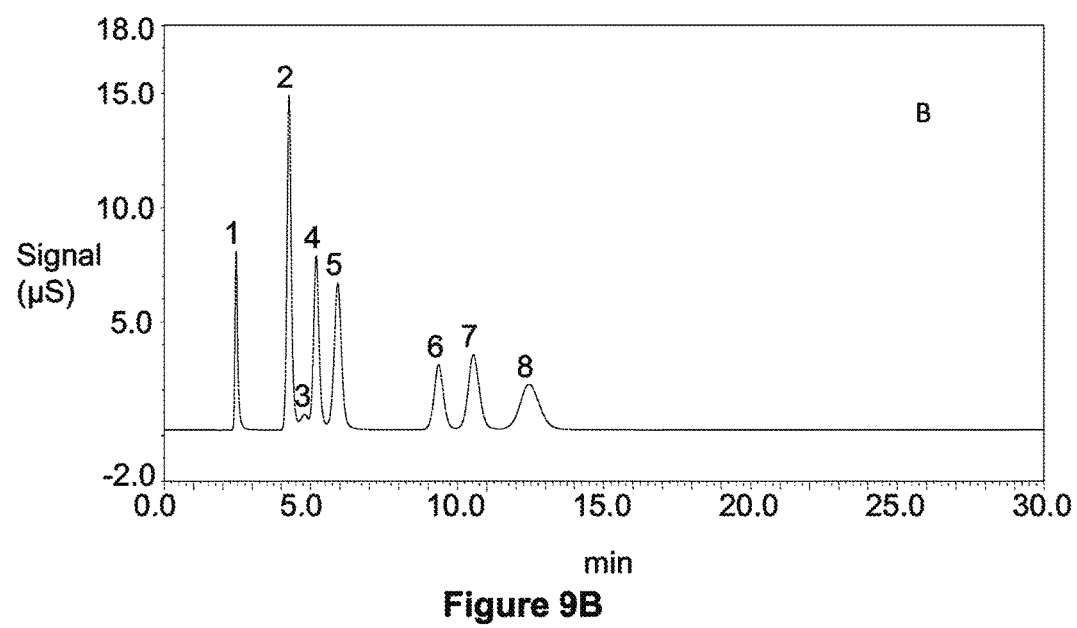

FIG. 9 shows separation of a test mixture of seven anions is shown above using a current setting of 29 mA (A) and 21 mA (B) using the suppressor device of the present invention.

Example 3

A 4 mm cation self-regenerating suppressor (CSRS) was assembled and plumbed following the schematic of FIG. 2. The anion exchange resin used was AG1 resin, 8% cross-linked with a capacity of 1.2 meqv/mL (Particle diameter 45-106 µm) sold by Bio-Rad, Hercules, Calif. Approximately 0.4 g was placed along the eluent channel in a dry form. Anion exchange screens were placed in the regenerant channels. Once the device was assembled and the device was hydrated it was ready for use. The static capacity was measured and was roughly 1.8 meqv for the eluent channel that included the exchange capacity of the ion exchange membranes and the ion exchange resin. The static capacity of a standard commercial suppressor sold under the name 4 mm CSRS 300 was roughly 600 µeqv. The device of the present invention had roughly a greater than 3 fold higher capacity than the prior art. The device was used as a suppressor for cation analysis using an IonPac CS12A (4×250 mm) column from Thermo Fisher Scientific. The eluent used was 20 mM methanesulfonic acid which was generated by an eluent generator module. The flow rate was 1 ml/min. In this example the CSRS 300 performance was compared at the recommended current as per Chromeleon recommendations which was 59 mA. The suppressor of the present invention was tested at 59 mA followed by testing at lower current settings. The device was run overnight for several runs to ensure that the current was sufficient for suppression. The suppressor was able to suppress the eluent at a current efficiency of near 100% with a current of 32 mA. The performance of the suppressor response with a CSRS 300 suppressor at the recommended current setting of 59 mA (3.11 V) was compared with the suppressor of the present invention at a setting of 32 mA (2.85 V) is shown in Table 3. These results illustrate that the suppressor is providing consistent response and is highly current efficient as evident from complete suppression at a current setting of 32 mA which is calculated as near 100% current efficiency. The static capacity of the device is also significant when compared to the CSRS 300 suppressor of the prior art. The device of the present invention also showed a 51% lower wattage than the recommended setting illustrating the benefit of operating the device at the current efficient regime.

TABLE 3

Peak response comparison between the CSRS 300 (commercial suppressor) operated at 59 mA and the device of the present invention that is operated at near 100% current efficient setting of 32 mA.
Peak Response (Area units)

| | | CSRS 300 59 mA | Present Invention 32 mA |
|---|---|---|---|
| 1 | Lithium | 0.361 | 0.360 |
| 2 | Sodium | 0.460 | 0.459 |
| 3 | Ammonium | 0.499 | 0.563 |
| 4 | Potassium | 0.758 | 0.758 |
| 5 | Magnesium | 1.080 | 1.064 |
| 6 | Calcium | 1.401 | 1.383 |

Figures 10A, 10B:
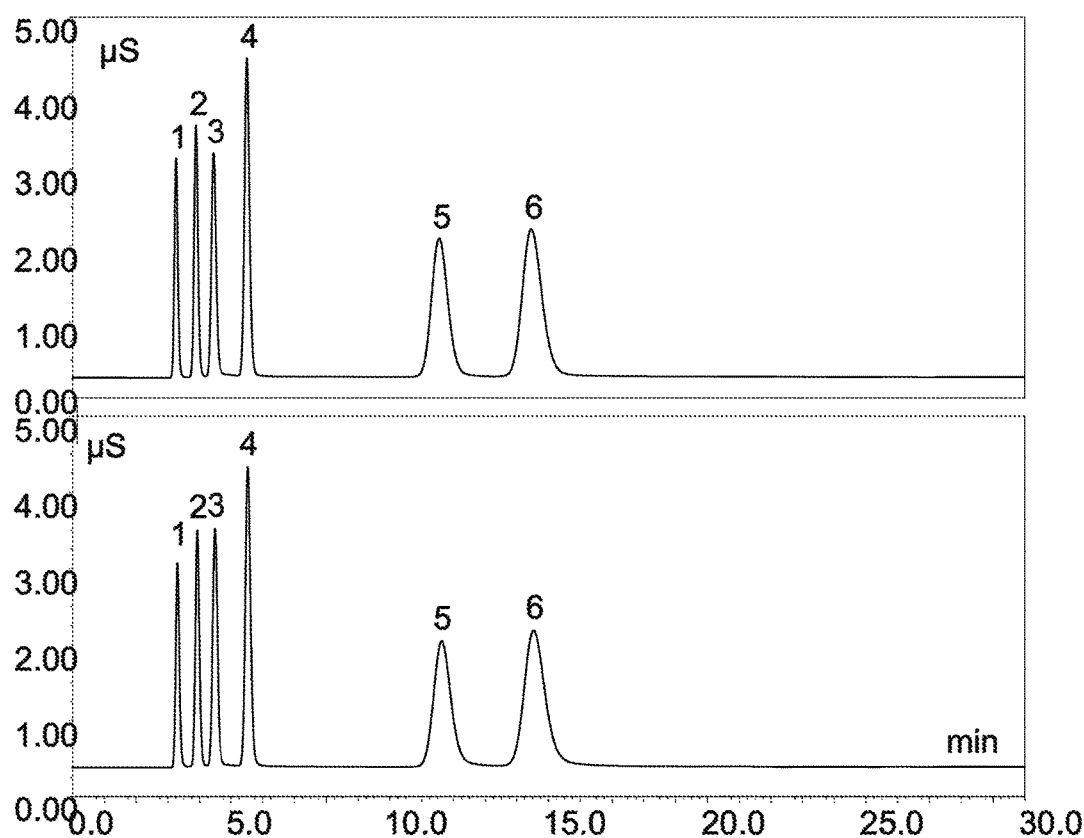

FIG. 10 shows separation of a test mixture of six cations is shown above using a standard CSRS 300 (A) at a current setting of 59 mA and a device of the present invention (B) at a current setting of 32 mA.

Example 4

The suppressor device of the present invention from Example 1 was used with carbonate/bicarbonate chemistry. The column was an IonPac AS22 (4×250 mm) and operated with an eluent comprising of 4.5 mM sodium carbonate and 1.4 mM sodium bicarbonate at a flow rate of 1 ml/min. The peak to peak noise of this chemistry was in the 6 nS/cm regime with an applied current of 26 mA. The device when operated in the intermittent mode with the current turned off (FIG. 11A) resulted in a noise of about 0.6 nS/cm. In this example the suppressor was powered for only 2 minutes with a 2 minute equilibration to reduce the baseline drift at the start of the run. Almost a 10 fold reduction in noise was feasible. The device was also operated in a mode where a small current of 1 mA was applied as shown in FIG. 11B. In this example the suppressor was powered for only 2 minutes and the current was switched to 1 mA to ensure suppressor directionality. Under these conditions the noise was also 0.6 nS/cm. Thus applying a small current did not influence the noise as per the present invention. Thus a 10 fold reduction in noise is feasible with the present invention. The baseline drift was 10% lower with the application of a small current as per the present invention. The high static capacity of the suppressor device and the high current efficiency allowed good regeneration of the suppressor device.

Figure 11A:
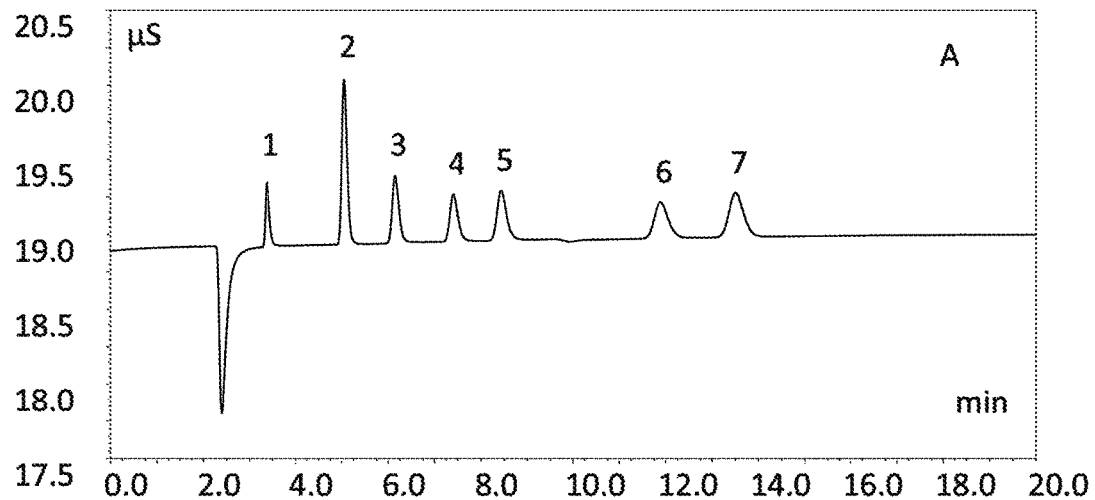
Figure 11B:
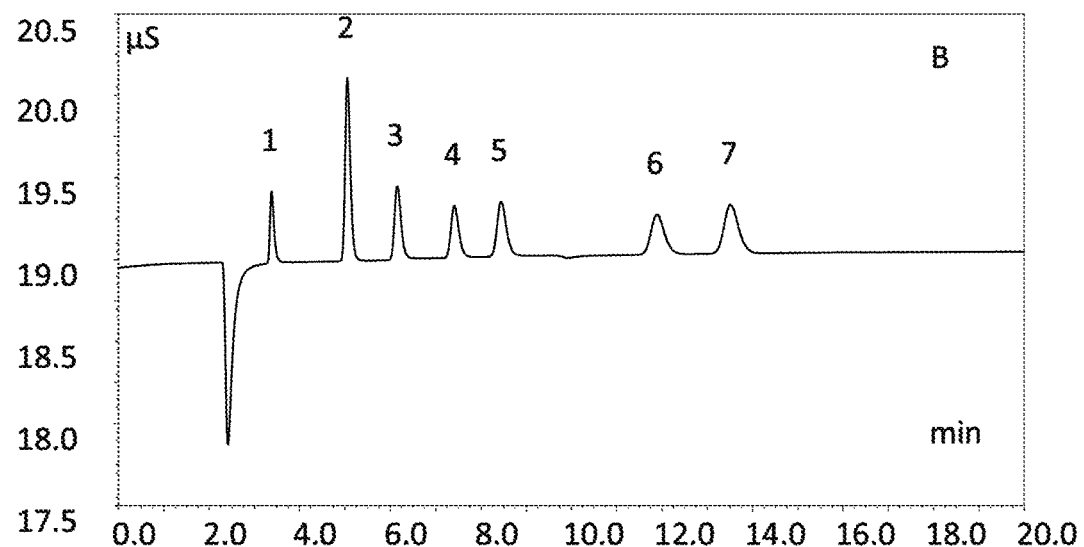

FIG. 11 shows separation of a test mixture of seven anions is shown above in the intermittent mode of operation. In FIG. 11A, the suppressor was operated for 20 minutes without current with a prior 2 minute regeneration at 300 mA followed by a 2 minute equilibration with the power off. In FIG. 11B, the suppressor was operated for 20 minutes with a current of 1 mA with a prior 2 minute regeneration at 300 mA followed by a 2 minute equilibration at 1 mA.

While the previous description herein has described the implementation of a suppressor using two or three chambers, it should be understood that this description is provided by way of example only, and does not limit the invention to a particular number of chambers. Those skilled in the art will recognize that embodiments of the invention may be beneficially incorporated into a number of architectures that include four or more chambers.

What is claimed is:

1. Apparatus for treating an aqueous stream, said apparatus comprising a first ion exchange membrane having exchangeable ions of a first charge and capable of allowing ions of said first charge to pass through said first ion exchange membrane, an aqueous stream flow channel having an inlet and an outlet, an ion receiving flow channel adjacent to said aqueous stream flow channel and separated therefrom by said first ion exchange membrane, stationary flow-through ion exchange packing of a same charge as said first ion exchange membrane disposed in said ion receiving flow channel, a packed bed of ion exchange particles disposed in said aqueous stream flow channel and extending at least partially between said aqueous stream flow channel inlet and outlet, a portion of said packed bed being packed at a density between about 1 gram of packed dry particles per cubic centimeter (cc) of said aqueous stream flow channel and less than 2 grams of said packed dry particles per cubic centimeter (cc) of said aqueous stream flow channel, said packed bed portion extending from said aqueous stream flow channel outlet upstream to at least 30% of a distance between said aqueous stream flow channel inlet and outlet, and first and second electrodes being in electrical communication with said aqueous stream flow channel and said ion receiving flow channel, respectively, in which a current efficiency of said apparatus when used as a suppressor is at least 75%.

2. The apparatus of claim 1 in which said aqueous stream is a sample stream including analyte ions and matrix ions of opposite charge to said analyte ions, said aqueous stream flow channel comprising an aqueous sample stream flow channel.

3. The apparatus of claim 2 in which said aqueous sample stream flow channel has an upstream portion, in which said sample stream contains matrix ions and an adjacent downstream portion in which said matrix ions have been suppressed.

4. The apparatus of claim 1 in which an ion exchange capacity of said ion exchange particles is at least 0.3 meqv/mL.

5. The apparatus of claim 1 in which said ion exchange particles have a size range of 1 to 200 μm.

6. The apparatus of claim 1 in which an electrical conductivity between said first and second ion exchange membranes through said ion exchange particles in said bed is discontinuous at said aqueous stream flow channel outlet.

7. Apparatus for treating an aqueous stream, said apparatus comprising a first ion exchange membrane having exchangeable ions of a first charge and capable of allowing ions of said first charge to pass through said first ion exchange membrane, an aqueous stream flow channel having an inlet and an outlet, an ion receiving flow channel adjacent to said aqueous stream flow channel and separated therefrom by said first ion exchange membrane, a second ion exchange membrane of a same type as said first ion exchange membrane and disposed adjacent a side of said aqueous stream flow channel opposite from said first ion exchange membrane, an ion source flow channel separated from said aqueous stream flow channel by said second ion exchange membrane, stationary flow-through ion exchange packing of a same charge as said first ion exchange membrane disposed in said ion receiving flow channel, a packed bed of ion exchange particles disposed in said aqueous stream flow channel and extending at least partially between said aqueous stream flow channel inlet and outlet, a portion of said packed bed being packed at a density between about 1 gram of packed dry particles per cubic centimeter (cc) of said aqueous stream flow channel and less than 2 grams of said packed dry particles per cubic centimeter (cc) of said aqueous stream flow channel, said packed bed portion extending from said aqueous stream flow channel outlet upstream to at least 30% of a distance between said aqueous stream flow channel inlet and outlet, and first and second electrodes being in electrical communication with said aqueous stream flow channel and said ion receiving flow channel, respectively, in which a current efficiency of said apparatus when used as a suppressor is at least 75%.

8. The apparatus of claim 7 in which a static ion exchange capacity of said first and second ion exchange membranes and said packed bed for said aqueous stream flow channel is at least 3 meqv/mL of an aqueous stream flow channel volume.

9. The apparatus of claim 7 in which said current efficiency of said apparatus when used as a suppressor is at least 90%.

10. A method for treating an aqueous stream including analyte ions of one charge and matrix ions of opposite charge to said analyte ions using an apparatus for treating said aqueous stream including said analyte ions and said matrix ions of opposite charge to said analyte ions, said apparatus comprising a first ion exchange membrane having exchangeable ions of a first charge and capable of allowing ions of said first ion exchange membrane to pass through said first ion exchange membrane, in which the first charge is of a same charge as said matrix ions, an aqueous stream flow channel having an inlet and an outlet, an ion receiving flow channel adjacent to said aqueous stream flow channel and separated therefrom by said first ion exchange membrane, stationary flow-through ion exchange packing of a same charge as said first ion exchange membrane disposed in said ion receiving flow channel, a packed bed of ion exchange particles disposed in said aqueous stream flow channel and extending at least partially between said aqueous stream flow channel inlet and outlet, a portion of said packed bed being packed at a density between about 1 gram of packed dry particles per cubic centimeter (cc) of said aqueous stream flow channel and less than 2 grams of said packed dry particles per cubic centimeter (cc) of said aqueous stream flow channel, said packed bed portion extending from said aqueous stream flow channel outlet upstream to at least 30% of a distance between said aqueous stream flow channel inlet and outlet, and first and second electrodes being in electrical communication with said aqueous stream flow channel and said ion receiving flow channel, respectively, in which a current efficiency of said apparatus when used as a suppressor is at least 75%, said method comprising flowing said aqueous stream through said aqueous stream flow channel;

simultaneously flowing an ion receiving stream through said ion receiving flow channel;

suppressing said matrix ions; and regenerating said first ion exchange membrane, said aqueous stream flow channel having an upstream portion containing said matrix ions and an adjacent downstream portion in which said matrix ions have been suppressed.

11. The apparatus of claim 1 in which said current efficiency of said apparatus when used as a suppressor is at least 90%.

12. The method of claim 10 in which said current efficiency of said apparatus when used as a suppressor is at least 90%.

13. The method of claim 10 in which a current is passed between said first and second electrodes.

14. The method of claim 13 in which said current is passed during suppression and regeneration.

15. The method of claim 13 in which said current is passed during regeneration of said first ion exchange membrane but not during suppression of said matrix ions.

16. The method of claim 10 in which said apparatus further comprises a second ion exchange membrane of a same type as said first ion exchange membrane adjacent an opposite side of said aqueous stream flow channel from said first ion exchange membrane and an ion source flow channel separated from said aqueous stream flow channel by said second ion exchange membrane.

17. The method of claim 16 in which a static ion exchange capacity of said first and second ion exchange membranes and said packed bed for said aqueous stream flow channel is at least 3 meqv/mL of an aqueous stream flow channel volume.

18. The method of claim 10 in which an ion exchange capacity of said ion exchange particles is at least 0.3 meqv/mL.

19. The method of claim 10 in which said ion exchange particles have a size range of 1 to 200 μm.

20. The method of claim 10 in which an electrical current between said first and second ion exchange membranes through said ion exchange particles in said bed at said aqueous stream flow channel outlet is discontinuous.

* * * * *